United States Patent [19]
Wu et al.

[11] Patent Number: 5,753,444
[45] Date of Patent: May 19, 1998

[54] METHODS AND KITS USING INOSINE-CONTAINING PROBES FOR DISCRIMINATING VARIANT NUCLEIC ACID SEQUENCES

[75] Inventors: Linxian Wu, Sandy; Jana Coombs; Sharon L. Malmstrom, both of Salt Lake City; Michael J. Glass, Centerville, all of Utah

[73] Assignee: Gull Laboratories, Inc., Salt Lake City, Utah

[21] Appl. No.: 689,235

[22] Filed: Aug. 7, 1996

Related U.S. Application Data

[62] Division of Ser. No. 587,209, Jan. 16, 1996, Pat. No. 5,612,473.

[51] Int. Cl.$^6$ .............................. C12Q 1/68; C07H 21/04
[52] U.S. Cl. .................................................. 435/6; 536/24.3
[58] Field of Search ........................ 435/6, 810; 536/24.3

[56] References Cited

U.S. PATENT DOCUMENTS

| | | | |
|---|---|---|---|
| 4,898,825 | 2/1990 | Morii et al. | 435/212 |
| 4,935,342 | 6/1990 | Seligson et al. | 435/6 |
| 4,965,188 | 10/1990 | Mullis et al. | 435/6 |
| 5,304,466 | 4/1994 | De Leys et al. | 435/5 |
| 5,453,355 | 9/1995 | Birkenmeyer et al. | |
| 5,459,034 | 10/1995 | Tabaqchali et al. | |
| 5,514,571 | 5/1996 | Raibowol | 435/172.3 |
| 5,532,138 | 7/1996 | Singh et al. | 453/7.93 |
| 5,567,809 | 10/1996 | Apple et al. | 536/24.3 |

FOREIGN PATENT DOCUMENTS

| | | |
|---|---|---|
| 0 332 435 | 9/1989 | European Pat. Off. |
| WO 93/09250 | 5/1993 | WIPO |
| WO 94/28177 | 12/1994 | WIPO |

OTHER PUBLICATIONS

Ehlen et al., Biochem. Biophys. Res. Comm. 160(2), 441–447 (1989).

Saiki et al., Nature 324, 163–166 (1986).

Martin et al., Nucleic Acids Res. 13(24), 8927–8938 (1985).

Wu, L., McCarthy, B.J., Kadushin, J.M., Nuss, C.E., *A Simple and Economic Method for Directly Performing PCR on Washed Blood Cells or on Whole Blood*, Transgenica, 1994; 1(1): 1–5.

Wu., L., Chaar, O., Bradley, K., Kadushin, J., *HLA DR DNA Typing With a Microtiter Plate–Based Hybridization Assay*, Hum. Immun. 1993; 37: p. 141.

Bauer, H., Ting., Y., Greer, C., Chambers, J., Tashiro, C., Chimera, J., Reingold, A., Monos, M., JAMA 265:472–477 (1991), *Genital Human Papillomavirus Infection in Female University Students and Determined by a PCT–Based Method*.

Nuijten, P., Van Asten, F., Gaastra, W., Van Der Zeijst, B., J. Biol. Chem. 265:17798–17804 (1990), "Structural and Functional Analysis of Two Campylobacter jejuni Flagellin Genes".

Stone, G., Oberts, R., Hays, M., McVey, S., Chengappa, M., J. Clin. Microbiol. 32:1742–1749 (1994), *Detection of Salmonella Serovars from Clinical Samples by Enrichment Broth Cultivation–PCR Procedure*.

Galan, J., Ginocchio, C., Costeas, P., J. Bacteriol. 174:4338–4348 (1992), *Molecular and Functional Characterization of the Salmonella Invasion Gene invA; Homology of InvA to Members of a New Protein Family*.

Sakai, T., Saskawa, C., Makiro, S., Yoshikawa, M., Infect. Immun. 54:395–402 (1986), *DNA Sequence and Product Analysis of the virF Locus Responsible for Congo Red Binding and Cell Invasion in Shigella flexneri 2a*.

Yavzori, M., Cohen, D., Wasserlauf, R., Ambar, R., Rechavi, G., Ashkenazi, S., Eur. J. Clin. Microbiol. Infect. Dis. 13:232–237 (1994), *Identification of Shigella Species in Stool Specimens by DNA Amplification of Different Loci of the Shigella Virulence Plasmid*.

Yi–Kun, L., Qin, H., Molodysky, E., Morris, B., J. Virol. Methods 44L77–78 (1994), *Simple Microwave and Thermal Cycler Boiling Methods for Preparation of Cervicovaginal Lavage Cell Samples Prior to PCR for Human Papillomavirus Detection*.

Ohhara, M., Kursou, Y., Esumi, M., Biotechniques 17:726–728 (1994), *Direct PCT of Whole Blood and Hair Shafts by Microwave Treatment*.

(List continued on next page.)

*Primary Examiner*—Kenneth R. Horlick
*Attorney, Agent, or Firm*—Workman, Nydegger & Seeley

[57] ABSTRACT

The present invention provides methods and apparatus for detecting and discriminating multiple analytes within a test sample which are simple, user-friendly, cost-effective and fast. In particular, it is preferred that the overall time for sample preparation, nucleic acid sequence amplification, and nucleic acid sequence differentiation be about 5 hours or less. The methods of the present invention comprise (i) rapid sample processing means for rapidly preparing sample material of various types for amplification of nucleic acid sequences using unique nucleic acid extraction buffer formulations, (ii) multianalyte non-preferential amplifying process means for simultaneously and non-preferentially amplifying multiple target nucleic acid sequences, if present within the sample, using appropriate primer oligonucleotides optimized to achieve substantially similar amplification efficiencies, and (iii) multianalyte recognition process means for detecting and discriminating amplified nucleic acid sequences which incorporate nucleic acid sequence mismatch detection means for differentiating minor mismatches between multiple amplified nucleic acid sequences, including only single base mismatches, using appropriate probe oligonucleotides modified with neutral base substitution molecules. The processing kit products in accord with the present invention may incorporate all, or only some, of the above-described means.

2 Claims, No Drawings

OTHER PUBLICATIONS

Singh, R.K., Tell, S.G., White, C.T., Hoffman, D., Chi, V.L. & Erickson, B.W. (1993), *A Scalable Systolic Multiprocessor System for Analysis of Biological Sequences.* Research on Integrated Systems: Proceeding of the 1993 Symposium, MIT Press, Cambridge, MA, 168–182.

Cebula, T., Payne, W., Feng, P. J. Clin. Microbiol. 33:248–250 (1995), *Simultaneous Identification of Strains of Escherichia coli Serotype O157:H7 and Their Shiga–Like Toxin Type of Mismatch Amplification Mutation Assay–Multiplex PCR.*

Nakajima, H., Inoue, M., Mori, T., Itoh, K., Arakawa, E., Watanabe, H., J. Clin Microbiol. 30:2428–2486 (1992), *Detection and Identification of Yersinia Pseudotuberculosis and Pathogenic Yersinia enterocolitica by Improved Polymerase Chain Reaction Method.*

Wegmuller, B., Luthy, Jr. Candrian, U., Applied and Environmental Microbiology, 59:2161–2165 (1993), *Direct Polymerase Chain Reaction Detection of Camylobacter jejuni and Campylobacter coli in Raw Milk and Dairy Products.*

Chamberlain, J., Gibbs, R., Ranier, J., Caskey, C., *PCR Protocols: A Guide to Methods and Applications,* pp. 272–281.

Allard, Annika, et al., *Polymerase Chain Reaction for Detection of Adenoviruses in Stool Samples,* Journal of Clinical Microbiology, vol. 28, No. 12, pp. 2659–2667 (1990).

Ramotar, Karam, et al., *Direct Detection of Verotoxin–Producing Escherichia coli in Stool Samples by PCR,* Journal of Clinical Microbiology, vol. 33, No. 3, pp. 519–524 (1995).

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

TGAAATGGCA GAACAGCGTC    2 0

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

```
CGTTCTGAAC CTTTGGTAAT AAC                                                        23
```

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

```
GATGAGGAAG CTTTATATAC TTCG                                                       24
```

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

```
TGCATGATGC ATGCGAATAT CAA                                                        23
```

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

```
CAAAGTGGTT CTTATGCAAT GGC                                                        23
```

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

```
TGCTGCTGAG TTAATTCTAA GACC                                                       24
```

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
TGTGTACGCT GCGAGTGAAA                                                            20
```

(2) INFORMATION FOR SEQ ID NO:8:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:8:

GCCCCCAGTA ATCCATAAAG     20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

CTCTTCCATG GGTTTCTCAC     20

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

GATGCTCCAT CACTTCCTGA T     21

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

CAACTTCATC CACGTTCACC     20

( 2 ) INFORMATION FOR SEQ ID NO:12:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

AAGAGCCAAG GACAGGTAC     19

( 2 ) INFORMATION FOR SEQ ID NO:13:

( i ) SEQUENCE CHARACTERISTICS:
        ( A ) LENGTH: 19 base pairs
        ( B ) TYPE: nucleic acid
        ( C ) STRANDEDNESS: single (D) TOPOLOGY: linear (i i) MOLECULE TYPE: DNA (x i) SEQUENCE DESCRIPTION: SEQ ID NO:13:

TGGTTGATTT CCTGATCGC                                                                 19

(2) INFORMATION FOR SEQ ID NO:14:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (i i) MOLECULE TYPE: DNA (x i) SEQUENCE DESCRIPTION: SEQ ID NO:14:

CTGATCAGAT AAGGAAGATT G                                                              21

(2) INFORMATION FOR SEQ ID NO:15:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (i i) MOLECULE TYPE: DNA (x i) SEQUENCE DESCRIPTION: SEQ ID NO:15:

AAACTTGGAA CACTTCTTGC T                                                              21

(2) INFORMATION FOR SEQ ID NO:16:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (i i) MOLECULE TYPE: DNA (x i) SEQUENCE DESCRIPTION: SEQ ID NO:16:

GGCAGTAATA AGTTTGGTCA T                                                              21

(2) INFORMATION FOR SEQ ID NO:17:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (i i) MOLECULE TYPE: DNA (x i) SEQUENCE DESCRIPTION: SEQ ID NO:17:

GGAATTGATC AGCGTTGG                                                                  18

(2) INFORMATION FOR SEQ ID NO:18:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (i i) MOLECULE TYPE: DNA (x i) SEQUENCE DESCRIPTION: SEQ ID NO:18:

CACAACTGTG TTCACTAGC                                                                                    19

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

GGAATTGATC AGCGTTGG                                                                                     18

( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

TGGAATTGAG CAGCGTTG                                                                                     18

( 2 ) INFORMATION FOR SEQ ID NO:21:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: N =INOSINE ( x i ) SEQUENCE DESCRIPTION: SEQ ID NO:21:

GTGGAATTNA GCAGCGTTG                                                                                    19

( 2 ) INFORMATION FOR SEQ ID NO:22:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: N =INOSINE ( x i ) SEQUENCE DESCRIPTION: SEQ ID NO:22:

GTGGAATTGA GNAGCGTTG                                                                                    19

( 2 ) INFORMATION FOR SEQ ID NO:23:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA

```
        ( i x ) FEATURE:
                ( A ) NAME/KEY: N =INOSINE ( x i ) SEQUENCE DESCRIPTION: SEQ ID NO:23:

GTGGAATTGA GCANCGTTG                                                                    19

( 2 ) INFORMATION FOR SEQ ID NO:24:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: linear ( i i ) MOLECULE TYPE: DNA ( i x ) FEATURE:
                ( A ) NAME/KEY: N =INOSINE ( x i ) SEQUENCE DESCRIPTION: SEQ ID NO:24:

TGTGNAATTN AGCANCGTTG GT                                                                22

( 2 ) INFORMATION FOR SEQ ID NO:25:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: linear ( i i ) MOLECULE TYPE: DNA ( i x ) FEATURE:
                ( A ) NAME/KEY: N =INOSINE ( x i ) SEQUENCE DESCRIPTION: SEQ ID NO:25:

TGTGGAATTN AGNANCGTTG GT                                                                22

( 2 ) INFORMATION FOR SEQ ID NO:26:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: DNA ( i x ) FEATURE:
                ( A ) NAME/KEY: N =INOSINE ( x i ) SEQUENCE DESCRIPTION: SEQ ID NO:26:

GGAATTNAGC AGCGTTGG                                                                     18

( 2 ) INFORMATION FOR SEQ ID NO:27:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: DNA ( i x ) FEATURE:
                ( A ) NAME/KEY: N =INOSINE ( x i ) SEQUENCE DESCRIPTION: SEQ ID NO:27:

GGAATTGAGN AGCGTTGG                                                                     18
```

( 2 ) INFORMATION FOR SEQ ID NO:28:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: N =INOSINE ( x i ) SEQUENCE DESCRIPTION: SEQ ID NO:28:

GGAATTNAGN AGCGTTGG                                               18

( 2 ) INFORMATION FOR SEQ ID NO:29:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: N =INOSINE ( x i ) SEQUENCE DESCRIPTION: SEQ ID NO:29:

TGTGGAATTG AGNAGCGTTG                                           20

( 2 ) INFORMATION FOR SEQ ID NO:30:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: N =INOSINE ( x i ) SEQUENCE DESCRIPTION: SEQ ID NO:30:

GTGGAATTGA GNAGCGTTGG                                           20

METHODS AND KITS USING INOSINE-CONTAINING PROBES FOR DISCRIMINATING VARIANT NUCLEIC ACID SEQUENCES

This application is a divisional of application Ser. No. 08/587,209, filed Jan. 16, 1996, U.S. Pat. No. 5,612,473.

BACKGROUND OF THE INVENTION

1. Technical Field

This invention relates to nucleic acid sequence based detection technology. In particular, the present invention relates to methods and apparatus permitting the detection and discrimination of multiple analytes within various types of sample material.

2. Background Information

Accurate detection of biological analytes present in various types of test samples is useful for many purposes including clinical, experimental, and epidemiological analyses. Because the genetic information in all living organisms is carried largely in the nucleic acids, either double-stranded deoxyribonucleic acid (DNA) or ribonucleic acid (RNA), detection and discrimination of specific nucleic acid sequences permits the presence, or absence, of a particular analyte within a test sample to be determined.

The development of the polymerase chain reaction (PCR) process for amplifying one or more targeted nucleic acid sequences within a sample or mixture of nucleic acid(s) has greatly facilitated processes for detecting and discriminating specific nucleic acid sequences. See, e.g., U.S. Pat. No. 4,965,188, the disclosure of which is herein incorporated by reference. For each target nucleic acid sequence to be amplified, the PCR process involves treating separate complementary strands of nucleic acid with two primers selected to be substantially complementary to portions of the target nucleic acid sequence within the two strands. The primers are extended with a thermostable enzyme to form complementary primer extension products which, when separated into their complementary strands, produce template strands for extending the complementary primer into the target nucleic acid sequence. The target nucleic acid sequences, when separated into their complementary strands, also act as templates for synthesis of additional target nucleic acid sequences. The steps of the PCR amplification process involve temperature cycling to effect hybridization of primers and templates, promotion of enzyme activity to enable synthesis of the primer extension products, and separation of the strands of the hybrids formed to produce additional template strands including strands of the synthesized target nucleic acid sequences. Each cycle exponentially increases the quantity of target nucleic acid sequences synthesized.

PCR amplification has proven useful in numerous clinical applications including the detection and/or diagnosis of infectious diseases and pathological genomic abnormalities as well as DNA polymorphisms that may not be associated with any pathological state. PCR amplification is particularly useful in circumstances where the quantity of the targeted nucleic acid is relatively small compared to other nucleic acids present in a sample, where only a small amount of the targeted nucleic acid is available, where the detection technique has low sensitivity, or where more rapid detection is desirable. For example, infectious agents may be accurately identified by detection of specific characteristic nucleic acid sequences. Examples of such infectious agents include bacteria such as Salmonella, Shigella, Chlamydia, and Neisseria, viruses such as the hepatitis virus, and parasites such as the malaria-causing Plasmodium. Because a relatively small number of pathogenic organisms may be present in a sample, the DNA extracted from these organisms typically constitutes only a very small fraction of the total DNA in the sample. Specific amplification of the characteristic DNA sequences, if present, greatly enhances the sensitivity and specificity of the detection and discrimination processes.

In addition, genetic sequences indicative of genetic disorders such as sickle cell anemia, $\alpha$-thalassemia, $\beta$-thalassemia, and cystic fibrosis can be amplified for detection. Detection of genes associated with disease states such as insulin-dependent diabetes or certain cancers is also useful. PCR amplification is particularly useful when the amount of nucleic acid available for analysis is very small such as in the prenatal diagnosis of genetic disorders using DNA obtained from fetal cells. The PCR amplification process has also enhanced the detection and discrimination of genetic variants which represent different alleles as, for example, HLA typing useful for determining compatibility of tissue for transplantation, disease susceptibility, and paternity.

PCR amplification is a powerful tool for the laboratory researcher. The procedures for preparing clinical samples to extract suitable nucleic acids or mixtures thereof, however, are typically difficult and time-consuming. For example, HLA typing usually requires purified genomic DNA as a template for the PCR process. Yet, it may be very difficult to extract and/or purify target nucleic acids, if present, in some types of sample material. Thus, the usefulness of PCR is limited in some circumstances although recent advances have been made. For example, it has been reported that it is possible to perform PCR directly on small samples of washed blood cells or whole blood by subjecting the samples to boiling in water for 10 minutes before conducting PCR. Wu, L., McCarthy, B. J., Kadushin, J. M., Nuss, C. E., *A Simple and Economic Method for Directly Performing PCR on Washed Blood Cells or on Whole Blood*, Transgenica, 1994: 1(1): 1–5. On the other hand, processing of other types of clinical samples such as, for example, stool samples, sputum samples, clotted blood samples and others, continues to be time consuming and difficult.

There are many circumstances where it would be useful to simultaneously detect and discriminate between multiple target nucleic acid sequences present or potentially present within a test sample. For example, an accurate diagnosis of an infectious disease may require determining which, if any, of numerous possible infectious agents are present in a clinical sample. Generally, the sample must be divided and multiple PCR amplification procedures must be separately performed with different primers, if available, for the different potential target nucleic acid sequences. This approach is very laborious. In addition, each PCR amplification process performed with available primers may yield a mixture of nucleic acids, resulting from the original template nucleic acid, the expected target nucleic acid sequence products, and various background non-target nucleic acid sequence products.

Although as many as three analytes have been simultaneously amplified by some methods, these methods also require difficult and time-consuming test sample preparation steps. A particular problem encountered when attempting to simultaneously amplify multiple targeted nucleic acid sequences is the phenomena of preferential amplification. Because different primers have different amplification efficiencies under the simultaneous processing conditions, preferential amplification results in disproportionate amplification of one or more target nucleic acid sequences such that the quantity of the preferentially amplified sequence(s) greatly exceeds the quantity of the other amplified sequences present. Another problem encountered during simultaneous amplification of multiple analytes is cross-reactivity. Significant sequence matches between the different primers can diminish amplification efficiency of the specific target nucleic acid sequence or cause a false positive amplification to occur. Thus, both preferential amplification and cross-reactivity must be prevented or minimized to permit accurate and efficient simultaneous analysis of multiple analytes.

Numerous methods for detecting and discriminating nucleic acid sequences using oligonucleotide probes, i.e., probes complementary to the PCR-amplified products, are known. Typically, a solid phase system is used. For example, either the PCR amplified products or the probes may be affixed directly onto a series of membranes. The non-affixed components, i.e., either the probes or the PCR products, respectively, are then added to the separate membranes under hybridization conditions. Either the probes or the PCR products are labeled with some type of label moiety so as to be detectable by spectroscopic, photochemical, biochemical, immunochemical, or chemical means. Examples of label moieties include fluorescent dyes, electron-dense reagents, enzymes capable of depositing insoluble reaction products or of being detected chromogenically, such as horseradish peroxidase or alkaline phosphatase, a radioactive label such as $^{32}$P, or biotin. Hybridization between the PCR products and probes will occur only if the components are sufficiently complementary to each other. After hybridization, a washing process removes any non-hybridized molecules so that detection of remaining labeled component indicates the presence of probe/target nucleic acid hybrids.

In addition to the classic dot-blot detection methods, solid-phase systems utilizing microtiter plates are also known. Various methods have been used to immobilize the desired component, either the probe or the PCR products, onto the microplate. In one approach, hydrophobic action passively adsorbs the component onto the microplate. Alternatively, the biotin/avidin interaction is utilized by, for example, incorporating biotin onto the component and passively absorbing avidin molecules onto the microplate such that the biotinylated components become bound to the avidin. A concern with these techniques, however, is that the hydrophobic binding used to immobilize the components to the plate is less efficient than desired. Only a relatively small quantity of component becomes bound to the plate and the hydrophobic binding may not withstand stringent hybridization or washing procedures such that some of the bound components or probe/nucleic acid complexes may be washed away during processing. The use of covalent linking chemistry has recently been shown to produce more consistent and efficient binding of oligonucleotide probes to microplate plastic surfaces. Wu, L., Chaar, O., Bradley, K., Kadushin, J., HLA DR DNA Typing With a Microtiter Plate-Based Hybridization Assay, Hum. Immun., 1993; 37: p. 141. In this technology, the oligonucleotide probes are attached covalently to chemical linkers on the plastic surface via the 5'-end phosphate group, amine group, or other reactive moiety. This approach does appear to improve efficiency while simplifying the procedure.

For some purposes, it is necessary to identify variations in nucleic acid sequences such as single or multiple nucleotide substitutions, insertions or deletions. These nucleotide variations may be mutant or polymorphic allele variations. Of particular interest and difficulty is the discrimination of single-base mismatched nucleic acid sequences. Sequence specific oligonucleotide probes, i.e., probes which are exactly complementary to an appropriate region of the target nucleic acid sequence, are typically used. All primers and probes, however, hybridize to both exactly complementary nucleic acid sequence regions as well as to sequences which are sufficiently, but not exactly, complementary, i.e., regions which contain at least one mismatched base. Thus, a specific probe will hybridize with the exact target nucleic acid sequence as well as any substantially similar but non-target nucleic acid sequences which are also present following the amplification process.

Various approaches to discriminating these similar hybrids from one another have been used. For example, it is known that the hybrids wherein the base-matching between the probe and nucleic acid sequence is exactly complementary, i.e., hybrids containing the exact target sequence, are bound together more strongly than are hybrids wherein the base matching is less than perfect. Accordingly, stringent washing conditions and/or processing with toxic chemicals are imposed to affect the physical properties of the hybrid complexes and, in theory, cause the weaker complexes to disassociate. These known methods for detecting nucleic acid sequence base mismatches are too difficult, harsh, and inconvenient for routine laboratory use.

In view of the foregoing, it would be advantageous to provide methods and apparatus for improving the efficiency and decreasing the time required to prepare and amplify multiple target nucleic acid sequences within a test sample by permitting various types of sample material to be prepared for DNA amplification without laborious nucleic acid extraction and purification steps.

It would be another advantage to provide methods and apparatus for improving the efficiency and decreasing the time required to prepare and amplify multiple targeted nucleic acid sequences within a test sample by permitting multiple target nucleic acid sequences within the sample to be simultaneously and non-preferentially amplified.

It would be another advantage to provide such methods and apparatus for improving the efficiency and decreasing the time required to prepare and amplify multiple targeted nucleic acid sequences within a test sample which are simple, user-friendly, cost-effective and fast.

It would be still another advantage to provide methods and apparatus for detecting and discriminating even single-base mismatches between multiple amplified nucleic acid sequences which do not require stringent, harsh, and inconvenient processing conditions.

SUMMARY OF THE INVENTION

It is a primary object of the present invention to provide methods and apparatus for improving the efficiency of detection and discrimination of multiple analytes within a test sample by permitting various types of sample material to be rapidly and simply prepared for nucleic acid amplification and by permitting multiple target nucleic acid sequences within a sample to be simultaneously and non-preferentially amplified.

It is another object of the present invention to provide methods and apparatus for detecting and discriminating multiple analytes within a test sample which are simple, user-friendly, cost-effective and fast. In particular, it is preferred that the overall time for sample preparation, nucleic acid sequence amplification, and nucleic acid sequence differentiation be about 5 hours or less.

It is an additional object of the present invention to provide such methods and apparatus which permit virtually any type of sample material to be simply and rapidly prepared for a nucleic acid amplifying process. In particular, it is desired to provide rapid sample processing means for preparing a sample which avoids laborious nucleic acid extraction and purification steps. Preferably, the time for performance of the rapid sample processing means is about 5 minutes or less.

It is still a further object of the present invention to provide methods and apparatus for detecting and discriminating multiple analytes within a test sample which permit multiple target nucleic acids to be simultaneously amplified in a non-preferential manner. In particular, it is desired to provide rapid and efficient multianalyte non-preferential amplifying process means for simultaneously and non-preferentially amplifying multiple target nucleic acid sequences, if present. Preferably, the time for performance of the multianalyte non-preferential amplifying process means is about 2 hours or less.

Yet another object of the present invention is to provide methods and apparatus for detecting and discriminating multiple analytes within a test sample which permits rapid and accurate detection and discrimination of target nucleic acid sequences. In particular, it is desired to provide multianalyte recognition process means which are simple, user-friendly, and rapid and which incorporate nucleic acid sequence mismatch detection means for discriminating between amplified nucleic acid sequences having minor base mismatches, including only a single base mismatch. Preferably, the time for performance of the multianalyte recognition process means, including nucleic acid sequence mismatch detection, if necessary, is about 2 hours or less.

These and other objects and advantages of the invention will be better understood by reference to the detailed description, or will be appreciated by the practice of the invention. To achieve the foregoing objects, and in accordance with the invention as embodied and broadly described herein, the methods of the present invention comprise (i) rapid sample processing means for rapidly preparing sample material of various types for amplification of nucleic acid sequences using unique nucleic acid extraction buffer formulations, (ii) multianalyte non-preferential amplifying process means for simultaneously and non-preferentially amplifying multiple target nucleic acid sequences, if present within the sample, using appropriate primer oligonucleotides optimized to achieve substantially similar amplification efficiencies, and (iii) multianalyte recognition process means for detecting and discriminating amplified nucleic acid sequences which incorporate nucleic acid sequence mismatch detection means for differentiating minor mismatches between multiple amplified nucleic acid sequences, including only single base mismatches, using appropriate probe oligonucleotides modified with neutral base substitution molecules.

The unique extraction buffer formulation of the rapid sample processing means is effective with substantially any type of sample material. Preferably, the time for performance of the sample processing means is about 5 minutes or less. The unique oligonucleotide primers of the multianalyte non-preferential amplifying process means are adapted to ensure that cross-reactivity is avoided and that amplification efficiency is substantially equal at the selected process conditions. Preferably, the time for performance of the multianalyte non-preferential amplifying process is about 2 hours or less. Preferably, the time for performance of the multiple analyte recognition process, including nucleic acid sequence mismatch detection, if necessary, is about 2 hours or less.

The apparatus of the present invention comprise processing kit products comprising means for (i) rapidly preparing virtually any type of sample material, using appropriate reagents, for nucleic acid sequence amplification, (ii) simultaneously and non-preferentially amplifying multiple target nucleic acid sequences, if present within the sample, using appropriate primer oligonucleotides, and (iii) detecting and discriminating multiple amplified nucleic acid sequences, including nucleic acid sequences having only single-base mismatches, using appropriate probe oligonucleotides. The processing kit products in accord with the present invention may incorporate all, or only some, of the above-described means.

DETAILED DESCRIPTION OF THE PREFERRED EMBODIMENTS

The present invention relates to methods and apparatus useful for detecting and discriminating multiple analytes potentially present within various types of sample materials. In particular, the methods and apparatus of the present invention utilize rapid sample processing means for preparing virtually any type of sample material for amplification of nucleic acid sequences contained therein, multianalyte non-preferential amplifying process means for simultaneously and non-preferentially amplifying multiple target nucleic acid sequences, if present, within the sample, and multianalyte recognition process means which incorporate nucleic acid sequence mismatch detection means for detecting and discriminating minor base mismatches, including single-base mismatches, between multiple amplified nucleic acid sequences.

The methods and apparatus in accord with the present invention permit detection and differentiation of multiple analytes within a sample to be performed within a relatively short time period, preferably less than about 5 hours. It is most preferred that the time for sample preparation be about 5 minutes or less, the time for simultaneous non-preferential amplification of the targeted nucleic acid sequences be about 2 hours or less, and the time for recognition of the multiple amplified nucleic acid sequences be about 2 hours or less.

The rapid sample processing means for preparing a sample for amplification of multiple nucleic acid sequences uses unique nucleic acid extraction buffer formulations effective with substantially any type of sample material. The multianalyte non-preferential amplifying process means utilizes multiple appropriate primer oligonucleotides optimized to ensure that cross-reactivity is avoided and that amplification efficiency is substantially equal at the selected process conditions. The multianalyte recognition process is performed with appropriate probe oligonucleotides and is preferably performed on microtiter plates incorporating covalent linking technology to enhance the binding efficiency of the probe/nucleic acid sequence hybrids. In addition, nucleic acid sequence mismatch detection means are provided to permit discrimination between amplified nucleic acid sequences having minor mismatches, including only single base mismatches. The nucleic acid sequence mismatch detection means utilize appropriate probe oligonucleotides modified by at least one neutral base substitution and do not require stringent or harsh processing conditions.

The apparatus of the present invention comprise processing kit products for detecting and discriminating multiple analytes within a test sample. The kit products comprise any or all of the following: (i) means for rapidly preparing virtually any type of sample material, using appropriate reagents, for nucleic acid sequence amplification, (ii) means for simultaneously and non-preferentially amplifying multiple target nucleic acid sequences, if present within the sample, using appropriate primer oligonucleotides, and (iii) means for detecting and discriminating multiple amplified nucleic acid sequences, including nucleic acid sequences having minor mismatches and even single base mismatches, using appropriate probe oligonucleotides.

One of the most important advantages of the methods and apparatus of the present invention is the time savings realized. The use of uniquely formulated extraction buffer solutions permits very rapid preparation of virtually any type of sample material. The use of uniquely optimized oligonucleotide primers ensures that preferential amplification is avoided and dramatically reduces the processing time for amplification of the target nucleic acid sequences by permitting amplification of multiple target nucleic acid sequences to proceed simultaneously. In accord with the present invention, as many as six different target nucleic acid sequences, and possibly more, can be non-preferentially amplified in one sample. Thus, a tremendous amount of time previously spent in preparing different types of sample materials and performing repetitive amplification processes on separate sample portions is saved in accord with the present invention. In addition, the unique probes used in the multianalyte recognition process may incorporate neutral base substitution means to facilitate accurate discrimination of nucleic acid sequences, including sequences having only a single base difference, even under simple and user-friendly processing conditions.

The methods and apparatus of the present invention are extremely versatile and have broad-reaching applications. For example, simultaneous detection of and discrimination between multiple potentially present microorganisms in biological samples permits rapid diagnosis of infections. It would also be useful to rapidly detect and discriminate between multiple potentially present microorganisms in other types of samples, such as foodstuffs, for various purposes such as diagnostic/forensic or quality control purposes. Applications in genetic research are also numerous and versatile. The detection and discrimination of specific genetic sequences, including discrimination between single base mismatched sequences, for purposes including diagnosing genetic disorders or identifying genetic variances, are rapidly, simply, and accurately performed in accord with the present invention.

The methods and apparatus of the present invention will be described both generally and with reference to a specific clinical application. One exemplary clinical application of the methods and apparatus of the present invention is the detection and discrimination among multiple potential infectious pathogens. In particular, the advantageous application of the methods and apparatus of the present invention in a Gastroenteritis Panel for assisting in diagnosing the cause of acute gastroenteritis through stool sample analysis will be described.

There can be many causes of acute gastroenteritis. It is often important to differentiate acute gastroenteritis from other conditions which may present similar signs and symptoms. In addition, it can be critical in some cases of infectious etiology to determine the specific causative agent. In some circumstances, rapid initiation of specific and effective pharmacologic therapy may be life-saving while, in other circumstances, use of inappropriate antimicrobial agents can actually be detrimental to the patient. Five groups of potential infectious etiological agents for which a rapid detection and discrimination analysis would be particularly helpful are Salmonella species, Shigella species and enteroinvasive *Escherichia coli*, Campylobacter species, enterohemorrhagic *E. coli* (particularly *E. coli* O157:H7), and *Yersinia enterocolitica*. Selected characteristics of these five groups are detailed below:

1. Salmonella species

| | |
|---|---|
| Disease: | Mild gastroenteritis to life threatening typhoid fever, bacteremia, meningitis, respiratory diease, cardiac diease and bone infections. Asymptomatic carrier state commmmon. |
| Prevalence: | Three million cases in U.S. estimated each year. Foodborne infection common. |
| Diagnosis: | Screened for using differential and moderately selective agar. Identified using biochemical battery and serotyping. |
| Time to preliminary test results: | 18–48 hours |
| Treatment: | Antibiotic therapy appropriate only in certain clinical circumstances-may be detrimental in other circumstances. Antibiotic resistance is common. |

Shigella species and enteroinvsive *E. coli* (EIEC)

| | |
|---|---|
| Disease: | Responsible for most cases of bacillary dysentry-watery diarrhea with blood and mmucus. Also associated with systemic infections leading to death. |
| Prevalence: | Most highly communicable of the bacterial diarrheas. Implicated in between 10 and 40 percent of diarrhea cases throughout the world. Often responsible for outbreaks in day-care centers. |
| Diagnosis: | Screened for using differential and moderately selective agar. Identified using biochemical battery and/or serotyping. |
| Time to preliminary test results: | 18–48 hours |
| Treatment: | Often resistant to sulfonamides, tetracyline, ampicillin, and trimethoprim-sulfamethoxazole. |

3. Campylobacter species

| | |
|---|---|
| Disease: | One of the most common causes of sporadic bacterial enteritis in the U.S. Systemic infections may occur. May mimic acute appendicitis resulting in unnecessary surgery. Guillain-Barré syndrome is strongly associated with infection. |
| Prevalence: | Over 2 million cases estimated to occur annually in developed nations. Many orders of magnitude higher in developing countries. Animal hosts common. |
| Diagnosis: | Usually requires microaerobic atmosphere and elevated temperature. Use selective media containing antimicrobials to inhibit normal flora. Identify using Gram stain and oxidase test. Can be sent to reference laboratory if further identification is needed. |
| Time to preliminary test results | 48–72 hours |
| Treatment: | Erythromycin and ciprofloxacin are usually drugs of choice. |

4. Enterohemorrhagic *E. coli* (EHEC) especially strain O157:H7

| | |
|---|---|
| Disease: | Associated with bloody and nonbloody diarrhea (hemorrhagic colitis), hemolytic-uremic syndrome (HUS - a major cause of acute renal failure in children), thrombotic thrombocytopenic purpura, and death. |
| Prevalence: | *E. coli* O157:H7 is estimated to cause more than 20,000 infections and as many as 250 deaths each year in U.S. Commonly associated with undercooked hamburger. |
| Diagnosis: | Does not ferment sorbitol rapidly—screen by using sorbitol-MacConkey agar (SMAC) plate. Assay for O157 antigen with antiserum. Send out to reference laboratory for H7 confirmation. |
| Time to preliminary test results: | 18–48 hours |
| Treatment: | Antibiotic treatment may make disease worse. |

5. *Yersinia enterocolitica*

| | |
|---|---|
| Disease: | A major cause of human gastroenteritis that can lead to serious systemic infections. Fatal cases of yersiniosis caused by transfusion of infected blood have been reported in several countries. |
| Prevalence: | Becoming increasingly important in U.S., Canada, and northern Europe. Commonly associated with foodborne epidemics. |
| Diagnosis: | Cultured at lower temperatures using selective medium such as CIN agar (cefsulodin-irgasan-novobiocin agar). Identified using biochemical batteries. Serologic assays may be useful. |
| Time to preliminary test results: | 24 hours to 7 days |
| Treatment: | Use of aminoglycosides and/or trimethoprim-sulfamethoxazole indicated in extra-intestinal cases. |

1. RAPID SAMPLE PROCESSING MEANS

It will be appreciated that the rapid detection and discrimination of the above potential pathogens would be extremely useful. Because acute gastroenteritis is localized in the gastrointestinal tract, the most appropriate sample material for analysis of potential pathogens is stool sample material. Prior art methods of analyzing stool sample material typically involve time-consuming and laborious handling and preparation processes. Detection and discrimination of pathogens present, if any, in stool sample material is typically challenging for the clinical laboratory. In accord with the methods and apparatus of the present invention, however, stool sample material is rapidly and simply prepared for subsequent nucleic acid sequence amplification, detection, and discrimination.

In accord with the present invention, it is desired to provide methods and apparatus which permit virtually any type of sample material to be simply and rapidly prepared for a nucleic acid amplifying process. Conventional techniques for extracting and/or purifying nucleic acids in various types of sample materials are generally time consuming and labor-intensive. In addition, it is very difficult, or impractical, to extract and/or purify nucleic acids within certain types of sample materials such as, for example, stool samples, blood samples containing different anticoagulants, or clotted blood samples. The present invention provides rapid sample processing means for preparing a sample for nucleic acid sequence amplification which avoids laborious nucleic acid extraction and purification steps. Preferably, the time for performance of the sample processing means is about 5 minutes or less.

The rapid sample processing means of the present invention utilize unique extraction buffer solutions to effect nucleic acid extraction in virtually any type of sample material. Known extraction buffer solutions typically comprise a buffer such as Tris-HCl (available from Sigma Chemical Co., St. Louis, Mo., USA), EDTA (ethylenediaminetetraacetic acid), and at least one detergent composition. In contrast, the inventive extraction buffer solutions comprise Tris-HCl, EDTA, at least one detergent, and at least one type of salt in a molar concentration, preferably in the range of 1M to 6M. Preferably, the inventive extraction buffer solution comprises two detergents such as, for example, Igepal CA 630 and Tween 20 (both available from Sigma Chemical Co., St. Louis, Mo., USA), and about 2.0M NaCl.

Example 1 compares the effectiveness of the inventive rapid sample processing means with two different conventional sample processing means for preparing stool samples for a nucleic acid amplification process referred to as phenol/chloroform extraction and protein salting-out. Performance time for the rapid sample processing means was approximately 3.5 minutes. In striking contrast, the performance time for the phenol/chloroform extraction was approximately 4.5 hours and the performance time for the protein salting-out method was approximately 12.75 hours. Example 2 illustrates the effectiveness of the inventive rapid sample processing means for sample materials other than stool samples.

EXAMPLE 1

MATERIALS AND METHODS

I. Samples

Clinical stool specimens were obtained from Utah State Health Laboratory, Salt Lake City, Utah; Medical University of South Carolina, Charleston, S.C.; Primary Children's Medical Center, Salt Lake City, Utah; and Laboratory Corporation of America, Salt Lake City, Utah. Pathogens were isolated by agar plate culture in all laboratories. All pathogenic isolates from specimens obtained from Laboratory Corporation of America were confirmed by Utah State Health Laboratory.

II. DNA Extraction From Clinical Stool Samples

A. Rapid Sample Processing Means (Approximate time: 3.5 minutes)

A 5% solution of well mixed clinical sample was prepared in a 2 ml microcentrifuge tube with 1000 μl of a preferred extraction buffer solution of the present invention comprising the following: 1% Igepal CA630, 0.5% Tween 20, 10 mM Tris-HCl, pH 8.0, 1 mM EDTA, and 2M NaCl (all chemicals obtained from Sigma Chemical Co., St. Louis Mo., USA). The mixture was strongly vortexed. The tube was centrifuged for 5 seconds at 16,000×g in an Eppendorf 5415 C microcentrifuge (Brinkman Instruments, Inc., Westbury, N.Y., USA). Eight hundred μl supernatant was transferred to a 2 ml microwaveable screw-cap centrifuge tube (Sarstadt, Newton, N.C., USA) and microwaved in a Kenmore 89250 microwave (Sears, Salt Lake City, Utah, USA) on high (~750 Watts) for 15 seconds, mixed, and microwaved 10 more seconds. After microwaving, the tube was centrifuged for 1 minute at 16,000×g to pellet precipitated protein. Without disturbing the pelletted material, a measured amount of supernatant was transferred to a new microcentrifuge tube, containing an equal volume of room temperature isopropanol (Sigma Chemical Co.) and mixed by vortexing. The tube was centrifuged for 1 minute at 16,000×g to pellet DNA. Supernatant was decanted and 1 ml 70% ethanol was added to pellet. Tube contents were vortexed and tube was centrifuged at 16,000×g for 1 minute. Without disturbing pellet, supernatant was removed by aspiration and 35 μl TE buffer (10 mM Tris-HCl, ph 8.0, 1 mM EDTA) was added to dissolve DNA.

Prepared samples were frozen at −20 degrees Celsius (° C.) until quantitation, purity and polymerase chain reaction (PCR) analysis were performed. B. Phenol/chloroform extraction (Approximate time: 4.5 hours)

A 5% solution of well mixed clinical stool sample was prepared in 1000 μl PBS, and mixed well by vortexing. The solution was centrifuged at 1750×g for 1 minute in an Eppendorf 5415 C microcentrifuge (Brinkman Instruments, Inc., Westbury, N.Y., USA) to pellet insoluble particulate material. Supernatant was transferred to a new microcentrifuge tube and centrifuged at 16,000×g for 5 minutes to pellet bacteria. Supernatant was removed and the pellet was resuspended in 100 μl phosphate buffered saline (PBS), pH 7.4.

Fifty μl Digestion/Lysis Buffer (50 mM Tris-HCl, pH 8.0, 100 mM EDTA, 100 mM NaCl, 3% sodium dodecyl sulfate (SDS), 2 mg/ml Proteinase K)(all chemicals obtained from Sigma Chemical Co.) was added to the tube and gently vortexed to mix. Sample was incubated for 2.5 hours at 55° C. and vortexed gently every 30 minutes. Phenol/ Chloroform/Isoamyl extraction was performed as follows: An equal volume of Phenol/Chloroform/Isoamyl alcohol (25:24: 1)(Sigma Chemical Co.) was added to the tube and mixed by inverting tubes 2–3 times. The organic and aqueous phases were separated by centrifugation at 1750×g for 15 minutes. The aqueous layer was transferred to a new microcentrifuge tube. The Phenol/Chloroform/Isoamyl extraction was performed three more times. Next, the same extraction procedure was performed twice more with Chloroform/Isoamyl alcohol (24:1 )(Sigma Chemical Co.). From the final extraction, the aqueous layer was transferred to a new tube and DNA was precipitated by adding an equal volume of room temperature isopropanol. The DNA was collected by centrifuging for 5 minutes at 16,000×g. The supernatant was removed and the DNA pellet was air dried for 15 minutes then resuspended in 35 μl TE buffer (10 mM Tris-HCl, ph 8.0, 1 mM EDTA) was added to dissolve DNA.

Prepared samples were frozen at −20 C. until quantitation, purity and polymerase chain reaction (PCR) analyses were performed.

C. Protein salting-out method (Approximate time: 12.75 hours)

A 5% solution of well mixed clinical stool sample was prepared in 1000 μl PBS, and vortexed well. The solution was centrifuged at 1750×g for 1 minute in an Eppendorf 5415 C microcentrifuge (Brinkman Instruments, Inc., Westbury, N.Y., USA) to pellet insoluble particulate material. Supernatant was transferred to a new microcentrifuge tube and centrifuged at 16,000×g for 5 minutes to pellet bacteria. Supernatant was removed and the pellet was resuspended in 300 μl Nuclei Lysis Buffer (10 mM Tris-HCl, pH 8.2, 400 mM NaCl, 2 mM EDTA)(all chemicals obtained from Sigma Chemical Co.) Lysate was digested overnight at 37° C. with 50 μl Digestion Solution (1% SDS, 2 mM EDTA, 1 mg/ml Proteinase K)(all chemicals obtained from Sigma Chemical Co.) and 20 μl 10% SDS (Sigma Chemical Co.). One hundred μl of 6M NaCl was added to the sample and the tube was vigorously shaken for 15 seconds, then centrifuged for 15 minutes at 1750×g. A measured amount of supernatant was transferred to a new tube. Exactly 2 volumes of room temperature absolute ethanol (Spectrum Chemical Mfg. Corp., Gardena, Calif., USA) was added and the tube was inverted several times. DNA was pelleted by centrifuging at 16,000×g for 15 minutes. Supernatant was removed by aspiration and 35 μl TE buffer (10 mM Tris-HCl, ph 8.0, 1.0 mM EDTA) was added to dissolve DNA.

Prepared samples were frozen at −20 C. until quantitation, purity and polymerase chain reaction (PCR) analyses were performed.

III. Spectrophotometric Quantitation and Purity Analysis

All DNA extractions were diluted 1:50 in purified water and absorbance was read at 260 nm and at 280 nm using a Hitachi U-3000 Spectrophotometer (Tokyo, Japan). Absorbance of the sample at 260 nm was used to calculate DNA concentration. The ratio of the absorbance readings at 260 nm and at 280 nm was used to determine purity of DNA in the sample. Because the quantities of PCR products were small, however, the sensitivity limits of the detection equipment were approached.

IV. PCR and Gel Detection

For amplification, a 50 μl reaction mixture was prepared using 5 μl of 10 X PCR buffer (Promega Corp., Madison, Wis., USA), 1 μl (5.0 U/μl) Taq polymerase, 1 μl (10 mM) each dNTP (Promega Corp., Madison, Wis., USA), 5 μl (400 ng total primer concentration) primers, 30 μl molecular grade water, and 5 μl (200 ng or less total DNA concentration) sample. Primer oligonucleotides, specific for the particular target nucleic acid sequences known to be present in the clinical samples were synthesized by Genosys Biotechnologies, Inc. (Woodlands, Tex., USA), Integrated DNA Technologies, Inc. (Coralville, Iowa, USA), Genemed Biotechnologies, Inc. (San Francisco, Calif., USA), and Cruachem, Inc. (Dulles, Va., USA).

PCR amplification was performed using a Perkin Elmer 9600 thermocycler (Norwalk, Conn., USA) with one denaturing cycle for 3 minutes at 96° C. followed by 35 cycles as follows: 30 seconds at 94° C. for denaturing, 20 seconds at 61° C. for annealing, 20 seconds at 72° C. for extension.

PCR products were visualized (and confirmed by size) by ethidium bromide staining after electrophoresis in 4% Nu Sieve 3:1 agar (FMC, Rockland, Md., USA). A 50–1000 bp ladder (Bio Ventures, Inc., Murfreesboro, Tenn., USA) was used as a molecular size marker.

RESULTS

Rapid Sample Processing Means Protocol Development

A. Microwave time

Microwave time was examined from 10 seconds to 180 seconds using 10% stool samples diluted two-fold (undilute to 1:1024) in 200 μl of the preferred extraction buffer solution of the present invention comprising the following: 1% Igepal CA630, 0.5% Tween 20, 10 mM Tris-HCl, pH 8.0, 1 mM EDTA, and 2M NaCl (all chemicals obtained from Sigma Chemical Co., St. Louis Mo., USA). Buffer solution temperature was measured using a Tegam Model 821 Microprocessor Thermometer (Salt Lake City, Utah, USA) after microwaving was completed. The following results were obtained:

TABLE 1

| | | Temperatures in Degrees Celsius | | | | | | | | | |
|---|---|---|---|---|---|---|---|---|---|---|---|
| Microwave Time (sec) | Dilutions: Non-dilute | 1:2 | 1:4 | 1:8 | 1:16 | 1:32 | 1:64 | 1:128 | 1:256 | 1:512 | 1:1024 |
| 10 | 48.2 | 54.0 | 46.4 | 43.9 | 44.7 | 47.5 | 42.9 | ND | ND | ND | 43.4 |
| 20 | 80.8 | 81.2 | 68.3 | 70.2 | 73.6 | 72.6 | 73.4 | ND | ND | ND | 69.9 |
| 30 | 90.6 | 91.6 | 91.2 | 80.1 | 87.5 | ND | ND | ND | ND | ND | ND |
| 40 | 95.3 | 98.2 | 94.8 | 91.1 | 93.7 | ND | ND | ND | ND | ND | ND |
| 50 | ~dry | 93.7 | 98.0 | 96.7 | 95.0 | ND | ND | ND | ND | ND | ND |
| 60 | dry | dry | 97.8 | 94.4 | 92.1 | ND | ND | ND | ND | ND | ND |

TABLE 1-continued

| | | Temperatures in Degrees Celsius | | | | | | | | | |
|---|---|---|---|---|---|---|---|---|---|---|---|
| Microwave Time (sec) | Dilutions: Non-dilute | 1:2 | 1:4 | 1:8 | 1:16 | 1:32 | 1:64 | 1:128 | 1:256 | 1:512 | 1:1024 |
| 90 | dry | dry | dry | dry | dry | 98.5 | 93.7 | ND | ND | ND | ND |
| 180 | dry | dry | dry | dry | dry | dry | dry | 98.3 | 97.2 | 95.3 | 98.1 |

ND = not done

Optimal microwave time of 20–30 seconds at high power (~750 Watts) was determined at a point where boiling temperatures were approximately met and where the sample did not lose appreciable volume or boil over. The microwave time was split during sample processing to optimize sample temperature and to lessen sample boil-over or explosion. A total of 15,000–22,500 Watt-seconds is preferred.

B. Centrifuge time

The time periods used to centrifuge samples during precipitation of protein and precipitation of DNA were examined at 1, 3, 5, 10, and 15 minutes. There were no marked differences in sample purity or DNA yield.

C. Ethanol vs. isopropanol precipitation

Absolute ethanol was compared to isopropanol for DNA precipitation. It was found that the use of isopropanol to precipitate DNA resulted in production of equal or greater quantities of PCR product during amplification, as visualized on ethidium bromide stained agarose gels, than the use of absolute ethanol. The use of isopropanol also generally resulted in equal or better absorbance ratios of extracted samples when compared to absolute ethanol. Isopropanol is easier to obtain than absolute ethanol. Also, only one (sample) volume of isopropanol is used to precipitate DNA compared to two (sample) volumes of absolute ethanol. Thus, isopropanol is more cost effective and preferred in the present invention.

Clinical Sample Analysis

A. Ratio of A260 nm/A280 nm

Spectrophotometric quantitation and purity analyses were performed as described above on nine clinical samples extracted according to the rapid sample processing means in accord with the present invention (method A) and nine samples prepared according to each of the conventional extraction methods, phenol/chloroform extraction (method B) and protein salting-out (method C). As shown in Table 2, the samples extracted with the rapid sample processing means of the present invention demonstrated comparable A260/A280 ratios to samples extracted with phenol/chloroform and better ratios than samples prepared by the protein salting-out method.

TABLE 2

| | A260/A280 Ratios | | | | | | | | | | |
|---|---|---|---|---|---|---|---|---|---|---|---|
| Method | 1 | 2 | 3 | 4 | 5 | 6 | 7 | 8 | 9 | Avg. | S.D. |
| A | 1.3 | 1.3 | 1.6 | 1.3 | 1.5 | 1.3 | 1.5 | 1.5 | 1.7 | 1.4 | 0.15 |
| B | 1.0 | 1.2 | 2.0 | 1.4 | 1.7 | 1.9 | 1.6 | 1.7 | 1.5 | 1.6 | 0.32 |
| C | 1.2 | 1.5 | 1.4 | 1.4 | 1.4 | 1.4 | 1.4 | 1.1 | 1.1 | 1.3 | 0.15 |

B. DNA Amplification and Gel Detection

PCR amplification and gel detection was performed as described above on nine clinical samples extracted according to the rapid sample processing means in accord with the present invention (method A) and nine samples prepared according to each of the conventional extraction methods, phenol/chloroform extraction (method B) and protein salting-out (method C). The samples extracted with the rapid sample processing means of the present invention demonstrated equal amplification efficiency when compared to samples subjected to phenol/chloroform extraction and better amplification efficiency than samples prepared according to the protein salting-out method.

EXAMPLE 2

The rapid sample processing means of the present invention constitutes a protein salting-out process accomplished by use of unique extraction buffer solutions. A preferred extraction buffer solution contains 1% Igepal CA-630, 0.5% Tween 20, 10 mM Tris-HCl, pH 8.0, 1 mM EDTA, and 2M NaCl. The rapid sample processing means of the present invention were developed for use with stool samples which are known to be one of the most difficult types of samples to prepare for nucleic acid amplification. The effectiveness of the rapid sample processing means for preparing stool samples is demonstrated in Example 1. In addition, the effectiveness of the rapid sample processing means in accord with the present invention for preparing other sample types including clotted blood samples, blood samples collected with different anticoagulants, sputum samples, tissue culture cells, and bacterial cultures has also been demonstrated.

For example, blood samples were collected from seven donors in Na Citrate, EDTA, heparin, and SST (clot) tubes. All samples were extracted in two trials using the method of the present invention. PCR amplification and gel detection demonstrated that all of these blood samples, regardless of collection type, amplified with β-globin primers. Similar results were obtained with sputum samples. Seven sputum samples, submitted for routine culture and/or Gram's stain to the Microbiology laboratory at Veterans Affairs Medical Center, Salt Lake City, Utah, were extracted using the method of the present invention and all of these samples amplified with β-globin primers.

2. MULTIANALYTE NON-PREFERENTIAL AMPLIFYING PROCESS MEANS

As reviewed in the background section, amplification of target nucleic acid sequences is utilized to facilitate detection and discrimination. Although there are several known techniques for nucleic acid sequence amplification, the polymerase chain reaction (PCR) amplification process has proven particularly useful in numerous clinical applications. Amplification of multiple analytes potentially present within a sample is generally accomplished by dividing the sample and performing multiple separate PCR amplification procedures on separate sample portions, each amplification procedure using a different primer pair specific for one of the different potential target nucleic acid sequences. It would be advantageous if multiple analytes could be amplified simultaneously. There are many circumstances where it would be useful to simultaneously detect and discriminate between multiple target nucleic acid sequences present or potentially present within a test sample. For example, an accurate diagnosis of an infectious disease may require determining which, if any, of numerous possible infectious agents are present in a clinical sample.

A particular problem encountered when attempting to simultaneously amplify multiple targeted nucleic acid sequences is the phenomena of preferential amplification. When attempting to simultaneously amplify multiple analytes, the primer pairs intended to amplify the different target nucleic acid sequences necessarily differ from each other. Different primers having different physical properties will have different amplification efficiencies under the selected simultaneous PCR process conditions. For example, it is known that primers having a higher content of guanosine and cytosine nucleotide bases, which form triple rather than double bonds, tend to anneal better during PCR. Other physical properties which affect the amplification efficiency include the primer melting temperature, the primer length, and the presence of hairpin loops or dimers. Process conditions which affect the amplification efficiency include the magnesium concentration, the particular polymerase enzyme employed, the enzyme concentration, the annealing temperature, and the primer concentration.

Preferential amplification results in disproportionate amplification of one or more target nucleic acid sequences such that the quantity of the preferentially amplified sequence(s) greatly exceeds the quantity of the other amplified sequences present. Another problem encountered during simultaneous amplification of multiple analytes is cross-reactivity among the primers. Significant sequence matches between the different primers can diminish amplification efficiency of the target nucleic acid sequence or cause a false positive amplification to occur. Thus, both preferential amplification and cross-reactivity must be prevented or minimized to permit accurate and efficient simultaneous analysis of multiple analytes.

The multianalyte nucleic acid sequence amplifying process of the present invention permits non-preferential amplification of multiple analytes within a sample to proceed simultaneously. The multianalyte non-preferential amplifying process means employs unique primer oligonucleotides optimized to ensure that cross-reactivity is avoided and that amplification efficiency is substantially equal at the selected process conditions. Preferably, the time for performance of the multianalyte non-preferential amplifying process is about 2.0 hours or less.

As illustrated in Example 3, for the gastroenteritis panel application, there are preferably six potential target nucleic acid sequences. Five are the potential pathogens, Salmonella, Shigella, E. coli, Campylobacter, and Yersinia microorganisms. A sixth is a control gene, β-globin, which should be present in every properly prepared sample.

EXAMPLE 3

MATERIALS AND METHODS
I. Bacterial Standards

DNA for bacterial standards was extracted from lyophilized American Type Culture Collection (ATCC) cultures, listed in Table 3, as follows: 300. μl of extraction buffer (10 mM Tris-HCl, pH 8.0, 1 mM EDTA, 1% Triton X-100, 0.5% Tween 20)(all chemicals obtained from Sigma Chemicals, St. Louis, Mo., USA) was added to each lyophilized vial. A 100 μl aliquot was microwaved for 3 minutes on the high setting (~750–775 watts). The DNA concentration was estimated spectrophotometrically then diluted to a working concentration of approximately 40 μg/ml.

TABLE 3

| ATCC STANDARD STRAINS | |
|---|---|
| BACTERIA | ATCC NUMBER |
| Salmonella typhimurium | 29946 |
| Shigella boydii | 29929, 9207, 8702, 9210, 8704, 12027, 9905, 12028, 49812, 12030, 12031, 12033, 12032, 12035, 12034 |
| Shigella dysenteriae | 9361 |
| Shigella flexneri | 29903 |
| Shigella sonnei | 29930, 29029, 29030, 29031, 25931 |
| Campylobacter coli | 33559 |
| Campylobacter feacalis | 33709 |
| Campylobacter fetus | 19438, 27374 |
| Campylobacter jejuni | 29428, 43431 |
| Campylobacter lari | 35221 |
| Campylobacter mucosalis | 43264 |
| Escherichia coli O157:H7 | 43894, 35150 |
| Escherichia coli O25:K98:NM | 43886 |
| Yersinia enterocolitica | 23715, 27729, 29913, 9610 |

The DNA sequences for the target regions of amplification for the six analytes are known and can be accessed from the Genbank with the nucleotide sequence accession numbers shown in Table 4.

TABLE 4

| NUCLEOTIDE SEQUENCE ACCESSION NUMBERS | |
|---|---|
| Salmonella | Genbank #M90846 |
| Campylobacter | Genbank #J05635 |
| Shigella/Enteroinvasive E. coli | Genbank #X16661 |
| Yersinia | Genbank #M29945 |
| Escherichia coli | Genbank #M14641 |
| β globin | Genbank #J00179, #J00093, #J00094, #J00096, #J00158, #J00159, #J00160, #J00161, #J00162, #J00163, #J00164, #J00165, #J00166, #J00167, #J00168; #J00169, #J00170, #J00171, #J00172, #J00178, #K01239, #K01890, #K02544, #M18047, #M19067, #M24868, #M24886, #X00423, #X00424, #X00672 |

II. Primer Oligonucleotides

Primer oligonucleotides were synthesized by Genosys Biotechnologies, Inc. (Woodlands, Tex., USA), Integrated DNA Technologies, Inc. (Coralville, Iowa, USA), Genemed Biotechnologies, Inc. (San Francisco, Calif., USA), and Cruachem, Inc. (Dulles, Va., USA). The original primer oligonucleotides were extensively modified to avoid cross-reactivity and to ensure non-preferential amplification. Presently preferred optimized primers are described in Tables 5 and 6.

TABLE 5

SELECTED PRIMER CHARACTERISTICS

| SEQ ID NO: | Primer Designation | Region | Map Position | Melting Temperature (°C.) | Product Length (bp) |
|---|---|---|---|---|---|
| 1 | SAL-1.4 | invE gene[1] | 18–37 | 59 | 469 |
| 2 | SAL-2.4 | invA gene[1] | 487–465 | 59 | |
| 3 | virF-1.3 | virF locus of | 623–646 | 59 | 215 |
| 4 | virF-2.1 | virulence plasmid[2] | 838–816 | 59 | |
| 5 | CFO3R.2 | flagellin | 1746–1771 | 60 | 340–360 |
| 6 | CFO4R | gene[3] | 2113–2090 | 60 | |
| 7 | YE1.1 | ail gene[4] | 547–566 | 59 | 287 |
| 8 | YE2 | | 834–815 | 59 | |
| 9 | ECO1.1 | uidA gene[5] | 198–217 | 59 | 423 |
| 10 | ECO2 | | 621–601 | 60 | |
| 11 | βglob-1 | human βglobin | 54–73 | 59 | 262 |
| 12 | βglob-2.1 | gene[6] | −195/−176 | 59 | |

[1]Stone, G., Oberst, R, Hays, M, McVey, S., Chengappa, M., Detection of Salmonella Serovars from Clinical Samples by Enrichment Broth Cultivation-PCR Procedure, J. Clin. Microbiol.; 32: 1742–1749 (1994).
[2]Yavzori, M., Cohen, D., Wasserlauf, R., Ambar, R., Rechavi, G., Ashkenazi, S., Identification of Shigella Species in Stool Specimens by DNA Amplification of Different Loci of the Shigella Virulence Plasmid, Eur. J. Clin. Microbiol. Infect. Dis.; 13:232–237 (1994).
[3]Wegmuller, B., Luthy, J., Candrian, U., Direct Polymerase Chain Reaction Detection of Campylobacter jejuni and Campylobacter coli in Raw Milk and Dairy Products, Applied and Environmental Microbiology; 59: 2161–2165 (1993).
[4]Nakajima, H., Inoue, M., Mori, T., Itoh, K., Arakawa, E., Watanabe, H., Detection and Identification of Yersinia pseudotuberculosis and Pathogenic Yersinia enterocolitica by Improved Polymerase Chain Reaction Method, J. Clin. Microbiol.; 30: 2484–2486 (1992).
[5]Cebula, T., Payne, W., Feng, P., Simultaneous Identification of Strains of Escherichia coli Serotype O157:H7 and Their Shiga-Like Toxin Type by Mismatch Amplification Mutation Assay-Multiplex PCR, J. Clin. Microbiol.; 33: 248–250 (1995).
[6]Bauer, H., Ting, Y., Greer, C., Chambers, J., Tashiro, C., Chimera, J., Reingold, A., Monos, M., Genital Human Papillomavirus Infection in Female University Students and Determined by a PCR-Based Method, JAMA; 265: 472–477 (1991).

TABLE 6

PREFERRED PRIMER SEQUENCES

| SEQ ID NO: | MODIFIED PRIMER SEQUENCE |
|---|---|
| 1 | 5'-TGAAATGGCAGAACAGCGTC-3' |
| 2 | 5'-CGTTCTGAACCTTTGGTAATAAC-3' |
| 3 | 5'-GATGAGGAAGCTTTATATACTTCG-3' |
| 4 | 5'-TGCATGATGCATGCGAATATCAA-3' |
| 5 | 5'-CAAAGTGGTTCTTATGCAATGGC-3' |
| 6 | 5'-TGCTGCTGAGTTAATTCTAAGACC-3' |
| 7 | 5'-TGTGTACGCTGCGAGTGAAA-3' |
| 8 | 5'-GCCCCCAGTAATCCATAAAG-3' |
| 9 | 5'-CTCTTCCATGGGTTTCTCAC-3' |
| 10 | 5'-GATGCTCCATCACTTCCTGAT-3' |
| 11 | 5'-CAACTTCATCCACGTTCACC-3' |
| 12 | 5'-AAGAGCCAAGGACAGGTAC-3' |

III. Probe Oligonucleotides

Internal probe oligonucleotides, complementary to one strand of the amplification products of the PCR reactions performed with the primers listed in Table 6, were obtained from Genosys Biotechnologies, Inc. (Woodlands, Tex., USA), Integrated DNA Technologies, Inc. (Coralville, Iowa, USA), Genemed Biotechnologies, Inc. (San Francisco, Calif., USA), and Cruachem, Inc. (Dulles, Va., USA). The probe designations and sequences are listed in Table 7.

TABLE 7

PROBE SEQUENCES

| SEQ ID NO: | Analyte | Probe Designation | Probe Sequence |
|---|---|---|---|
| 13 | Salmonella | SAL P.1 | 5'-TGGTTGATTTCCTGATCGC-3' |
| 14 | Shigella | SHIG P2.1 | 5'-CTGATCAGATAAGGAAGATTG-3' |
| 15 | Campylobacter | CAMP P.1 | 5'-AAACTTGGAACACTTCTTGCT-3' |
| 16 | Yersinia | YE P | 5'-GGCAGTAATAAGTTTGGTCAT-3' |
| 17 | Escherichia | ECO P1 | 5'-GGAATTGATCAGCGTTGG-3' |
| 18 | β-globin | βglob P.1 | 5'-CACAACTGTGTTCACTAGC-3' |

IV. Clinical Samples

Clinical stool samples were prepared in accord with the rapid sample processing means described above.

V. PCR Amplification

For amplification, a 50 µl reaction mixture was prepared using 5 µl of 10 X PCR buffer (Promega Corp., Madison, Wis., USA), 1 µl (5.0 U/µl) Taq polymerase, 1 µl (10 mM) each dNTP (Promega Corp., Madison, Wis., USA), 5 µl of mixed primers (890 ng total primer concentration as described below, see Table 8), 30 µl molecular grade water, and 5 µl (200 ng or less total DNA concentration) of ATCC strain DNA or clinical stool sample DNA. Due to the variability of β-globin DNA in clinical stool samples, control DNA was extracted from human cell lines (MOLT-4, HFF) and added with the primer mixture to each amplification reaction at a concentration of 0.1 µg/reaction.

PCR was performed using a Perkin Elmer 9600 thermocycler (Norwalk, Conn., USA) with one denaturing cycle for 3 minutes at 96° C. followed by 35 cycles as follows: 30 seconds at 94° C. for denaturing, 20 seconds at 61° C. for annealing, 20 seconds at 72° C. for extension.

VI. Gel Detection

PCR products were visualized (and confirmed by size) by ethidium bromide staining after electrophoresis in 4% Nu Sieve 3:1 agar (FMC, Rockland, Md., USA). A 50–1000 bp ladder (Bio Ventures, Inc., Murfreesboro, Tenn., USA) was used as a molecular size marker.

VII. Covalent Attachment of Nucleic Acid Probes

All probes were synthesized with a 5' terminal primary amine. N-oxysuccinimide amine binding microtiter plates (Corning Costar Corporation, Cambridge, Mass., USA) were used as the solid phase attachment support for the nucleic acid probes. Each probe was diluted to 1 µg/ml in phosphate buffered saline (PBS), pH 9.0, and 100 µl of each probe was placed in a separate well. The plate was incubated for 1 hour at room temperature. After incubation, the solution was aspirated and the plate washed 5 times with 300 µl wash buffer/well (2.0 mM Imidizole buffered saline, 0.02% Tween-20)(all chemicals obtained from Sigma Chemical Co., St. Louis, Mo., USA). The remaining active sites were blocked with Stabilcoat (BSI Corporation, Eden Prairie, Minn., USA) for 30 minutes at room temperature. The wells were aspirated and used directly for hybridization.

VIII. DNA Hybridization/Colorimetric Detection

Amplified products ($1 \times 10^{12}$ molecules) were diluted in 25 µl of PBS, pH 7.25, and added with 25 µl denaturing solution (0.8N NaOH) to a probe-coated well. After incubation for 10 minutes at room temperature, 25 µl 4X hybridization solution (PBS, pH 7.25, 8% BSA) and 25 µl neutralizing solution (4M Ammonium Acetate)(Sigma Chemical Co., St. Louis, Mo., USA) were added and incubated for a further 5 minutes at room temperature. The plate was then incubated for 45 minutes at 55° C. Following incubation, the plate was washed 5 times with wash buffer (1M Tris-buffered saline, pH 7.5, 1.0% Tween 20) at room temperature.

For colorimetric analysis of the hybridized products bound to the wells, 100 µl of streptavidin-alkaline phosphatase conjugate (SPA, Milan, Italy) was added and incubated for 30 minutes at 37° C. The plate was washed 5 times with wash buffer and incubated a further 30 minutes at 37° C. in 100 µl p-NPP solution (1 mg/ml p-nitrophenyl phosphate in 0.5M Tris, pH 9.5). The reaction was stopped with the addition of 1.5N NaOH. Absorbance values were determined by analysis at 405 nm on a SLT Labinstruments Model #16-886 microplate reader (SLT, Salzburg, Austria).

RESULTS

Primer Optimization

Oligonucleotide primers were designed to amplify all 5 analytes and β-globin internal control in a single PCR reaction tube. An analysis and modification of the original primers was undertaken with the objectives of improving the amplification efficiency of each primer and decreasing the possibility of cross-reactivity among the primer pairs. Several parameters were manipulated in order to minimize physical property differences among the primers. Each primer was modified to approximately the same length, i.e., 19–24 bp. Primer oligonucleotides of this length result in greater specificity in the amplification reaction while shorter primers may result in the amplification of non-specific products. Because the efficiency of the primer pairs is also effected by the presence of hairpin loops and dimers, OLIGO 5.0 software (NBI, Plymouth, Minn., USA) was used to analyze potential primers. If hairpin loops or dimers were found, the primer sequence was modified to remove them or to, at least, diminish the effect.

Cross-reactivity in a multiple primer reaction could also result in diminished amplification efficiency or in false positive amplifications. To analyze for cross-reactivity, a sequence alignment for each primer was performed using a BioSCAN database search of the Genbank. The computation was performed at the University of North Carolina, Chapel Hill, N.C., USA, using the BioSCAN network server. No significant sequence matches were reported. To further test for cross-reactivity, each primer pair was amplified with DNA from each of the six analytes. It was found that the Salmonella primers would amplify non specific products in a reaction with Molt 4 or HFF DNA, which were sources of β-globin DNA. To eliminate the cross-reactivity, new Salmonella primers were created by shifting the sequence several bases upstream or downstream from the original primer sequence. This shifting eliminated the cross-reactivity between the primers and the β-globin DNA.

In order to ensure that the primers are simultaneously annealing, the melting temperatures (Tm) need to be similar. Melting temperature for each primer was determined using the Physical Property Prediction software (Synthetic Genetics, Inc.) and the sequence was modified to obtain melting temperatures of 59°–60° C.

Preferential amplification in a multiple primer PCR process may occur due to competition for limited reagents in the reaction as well as efficiency of each primer to anneal to the target nucleic acid sequence. Since the reaction dynamics are different for each combination of primers, the optimum conditions need to be determined empirically. The six analyte simultaneous PCR process was optimized for magnesium concentration ($MgCl_2$ concentration in the buffer solution), Taq polymerase enzyme concentration, annealing temperature and primer concentration. PCR and gel detection was performed as each of these parameters were varied. Taq DNA polymerase was titrated from 2.0 U–5.5 U/reaction and the optimum concentration for this primer mix was determined to be 5.0 U/reaction. Magnesium concentrations were titrated from 1.0 mM to 6.0 mM and an optimum concentration of 1.5 mM was determined. Amplification annealing temperatures tested ranged from 53° C. to 63° C. Under these conditions, optimum amplification efficiency for all six analytes was achieved at 61° C. Primer concentration was modified for each primer pair in order to obtain equal efficiency. Under these selected optimum conditions, a preferred concentration of the modified primer pairs (SEQ ID NOS: 1–12) for each PCR reaction is shown in Table 8.

TABLE 8

A PREFERRED CONCENTRATION OF PRIMER PAIRS

| SEQ ID NOS: | Primer Pair Designations | Concentration (ng) of each Primer/each Primer Pair |
|---|---|---|
| 1,2 | Sal 1.4, Sal 2.4 | 200/400 |
| 3,4 | virF 1.3, virF 2.1 | 30/60 |
| 5,6 | CFO3R.2, CFO4R | 50/100 |
| 7,8 | YE 1.1, YE 2 | 75/150 |
| 9,10 | ECO 1.1, ECO 2 | 40/80 |
| 11,12 | β glob 1, βglob 2.1 | 50/100 |

Each primer pair was amplified individually, with 200 ng ATCC strain DNA (Table 3) and 200 ng of appropriate primer, to confirm amplification of the expected fragment size. For simultaneous multiple amplifications, 200 ng total concentration (40.0 ng of each bacterial analyte) of ATCC strain DNA, 0.1 µg of control (β globin) DNA, and 890 ng total concentration of primer mixture (Table 8) was used as the positive control. Clinical stool samples were amplified with 200 ng total (sample) DNA concentration, 0.1 µg of control (β globin) DNA, and 890 ng total primer mixture concentration (Table 8).

3. MULTIANALYTE RECOGNITION PROCESS MEANS/NUCLEIC ACID SEQUENCE MISMATCH DETECTION MEANS

As reviewed in the background section, numerous methods for detecting and discriminating nucleic acid sequences using oligonucleotide probes, i.e., probes complementary to the PCR-amplified products, are known. Either the probes or the PCR products are labeled with some type of label moiety so as to be detectable by spectroscopic, photochemical, biochemical, immunochemical, or chemical means. Examples of label moieties include fluorescent dyes, electron-dense reagents, enzymes capable of depositing insoluble reaction products or of being detected chromogenically, such as horseradish peroxidase or alkaline phosphatase, a radioactive label such as $^{32}P$, or biotin. The probes and PCR products are mixed under hybridization conditions such that hybridization occurs between the PCR products and probes which are sufficiently complementary to each other. After hybridization, processing to remove any non-hybridized molecules is performed such that detection of remaining labeled component indicates the presence of probe/target nucleic acid hybrids.

Typically, a solid phase system such as, for example, a microtiter plate having probe-coated wells, is used. In solid phase systems, an important factor affecting the efficiency of the detection process is the efficiency of the binding method used to immobilize the desired component, either the probe or the PCR products, onto the solid matrix. The use of covalent linking chemistry has recently been shown to produce more consistent and efficient binding of probe oligonucleotides to microplate plastic surfaces. In this technology, the oligonucleotide probes are attached covalently to chemical linkers on the plastic surface via a reactive moiety, such as an amine or phosphate group, attached to the 5'-end of the probe.

Also as reviewed in the background section, for some purposes, it is necessary to differentiate minor differences between amplified nucleic acid sequences such as nucleotide substitutions, insertions or deletions. These nucleotide variations may be mutant or polymorphic allele variations. Of particular interest and difficulty is the discrimination of single-base mismatched nucleic acid sequences. Sequence-specific oligonucleotide probes, i.e., probes which are exactly complementary to an appropriate region of the target nucleic acid sequence, are typically used. All primers and probes, however, hybridize to both exactly complementary nucleic acid sequence regions as well as to sequences which are sufficiently, but not exactly, complementary, i.e., regions which contain at least one mismatched base. Thus, a specific probe will hybridize with the exact target nucleic acid sequence as well as any substantially similar but non-target nucleic acid sequences which are also present following the amplification process.

Various approaches to discriminating these similar hybrids from one another have been used including, for example, stringent washing conditions and/or processing with toxic chemicals to affect the physical properties of the hybrid complexes. These known methods for detecting nucleic acid sequence base mismatches, however, are generally too difficult, harsh, and inconvenient for routine laboratory use.

The multianalyte recognition process of the present invention is performed with appropriate probe oligonucleotides and is preferably performed on microtiter plates incorporating covalent linking technology to enhance the binding efficiency of the probe/nucleic acid sequence hybrids. In addition, nucleic acid sequence mismatch detection means are provided to permit discrimination between amplified nucleic acid sequences having minor mismatches, including only single base mismatches. The nucleic acid sequence mismatch detection means utilize sequence-specific probe oligonucleotides incorporating neutral base substitution molecules, strategically positioned to discriminate the base differences of interest, to reduce the strength of the hybridization between any mismatched nucleic acid sequences and the probe. Because the mismatched sequence hybrids are thereby made significantly weaker than the matched sequence hybrids, differentiation of matched and mismatched hybrids is possible without the imposition of stringent or harsh processing conditions.

With respect to the gastroenteritis panel application, it is critical to be able to detect the presence of a highly virulent enterohemorrhagic strain of *E. coli* known as O157:H7. This virulent strain differs from other *E. coli* strains, represented by *E. coli* O025:K98:NM, by only a single base pair in the uidA gene. Because of the substantial similarity in nucleic acid sequences, both of these strains, if present, will amplify during a PCR amplification process using primers to target a nucleic acid sequence including the uidA gene. Thus, it is necessary to be able to distinguish whether the virulent O157:H7 strain is present in the PCR amplification products.

In accord with the present invention, this problem is solved through the use of modified sequence-specific probes which incorporate neutral base substitution molecules. In particular, as illustrated in Example 4, at least one inosine molecule is substituted, at a position other than the already present single-base mismatch, within probes otherwise sequence-specific for *E. coli* O157:H7. These modified probes ensure that the probe/O157:H7 strain nucleic acid sequence hybrids will match completely, except at the inosine location(s), while the probe/O25:K98:NM strain nucleic acid sequence hybrids will additionally mismatch at the single base mismatch location. Thus, the probe/ O25:K98:NM strain nucleic acid sequence hybrids are made weaker to thereby be sufficiently removable, without the use of harsh and inconvenient processing conditions or the use of toxic chemicals, to permit accurate discrimination between the single-base mismatched *E. coli* strains.

EXAMPLE 4

MATERIALS AND METHODS

I. Oligonucleotide Probes

Nucleic acid probes were synthesized by Genosys Biotechnologies, Inc (The Woodlands, Tex., USA). The single-base mismatched sequence-specific probes for the O25:K98:NM *E. coli* strain and for the virulent O157:H7 *E. coli* strain are shown in Table 9.

TABLE 9

SEQUENCE-SPECIFIC PROBES FOR TWO STRAINS OF *E. coli*

| SEQ: ID NO: | Probe Designation | *E. coli* Strain Specificity | Probe Sequence |
|---|---|---|---|
| 19 | M6 | O25:K98:NM | 5'- GGA ATT GAT* CAG CGT TGG-3' |
| 20 | M7 | O157:H7 | 5'-T GGA ATT GAG* CAG CGT TG-3' |

*single-base mismatch location

The sequences of the modified probes having at least one inosine (i) substitution are shown in Table 10.

TABLE 10

MODIFIED *E. coli* O157:H7 SEQUENCE-SPECIFIC PROBES

| SEQ ID NO: | Probe Designation | Probe Sequence |
|---|---|---|
| 21 | M1 | 5'- GT GGA ATT iAG CAG CGT TG-3' |
| 22 | M2 | 5'- GT GGA ATT GAG iAG CGT TG-3' |
| 23 | M3 | 5'- GT GGA ATT GAG CAi CGT TG-3' |
| 24 | M4 | 5'-TGT GiA ATT iAG CAi CGT TGG T-3' |
| 25 | M5 | 5'-TGT GGA ATT iAG iAi CGT TGG T-3' |
| 26 | M8 | 5'-    GGA ATT iAG CAG CGT TGG-3' |
| 27 | M9 | 5'-    GGA ATT GAG iAG CGT TGG-3' |
| 28 | M10 | 5'-    GGA ATT iAG iAG CGT TGG-3' |
| 29 | M11 | 5'-TGT GGA ATT GAG iAG CGT TG-3' |
| 30 | M12 | 5'- GT GGA ATT GAG iAG CGT TGG-3' |

II. Covalent Attachment of Nucleic Acid Probes

All probes were synthesized with a 5' terminal primary amine. N-oxysuccinimide amine binding microtiter plates (Corning Costar Corporation, Cambridge, Mass., USA) were used as the solid phase attachment support for the nucleic acid probes. Each probe was diluted to 1 µg/ml in phosphate buffered saline (PBS), pH 9.0, and 100 µl of each probe was placed in a separate well. The plate was incubated for 1 hour at room temperature. After incubation, the solution was aspirated and the plate washed 5 times with 300 µl wash buffer/well (2.0 mM Imidizole buffered saline, 0.02% Tween-20)(all chemicals obtained from Sigma Chemical Co., St. Louis, Mo., USA). The remaining active sites were blocked Stabilcoat (BSI Corporation, Eden Prairie, Minn., USA) for 30 minutes at room-temperature. The wells were aspirated and used directly for hybridization.

III. PCR Amplification

For amplification, a 50 µl reaction mixture was prepared using 5 µl of 10 X PCR buffer (Promega Corp., Madison, Wis., USA), 0.5 units Taq DNA polymerase, 200 µM each dNTP (deoxynucleotide triphosphate)(Promega Corp., Madison, Wis., USA), 200 ng of each primer specific for the uidA gene of *E. coli* (SEQ ID NOS: 9 and 10, see Table 6), and 200 ng of either *E. coli* O25:K98:NM (ATCC #43886, See Table 3) DNA or *E. coli* O157:H7 (ATCC # 35150, see Table 3) DNA. One primer, SEQ ID NO: 10, was biotinylated at the 5' terminal end.

PCR was performed using a Perkin Elmer 9600 thermocycler (Norwalk, Conn., USA) with one denaturing cycle for 3 minutes at 96° C. followed by 35 cycles as follows: 30 seconds at 94° C. for denaturing, 20 seconds at 61° C. for annealing, 20 seconds at 72° C. for extension.

IV. Gel Detection

PCR products were visualized (and confirmed by size) by ethidium bromide staining after electrophoresis in 4% Nu Sieve 3:1 agar (FMC, Rockland, Md., USA). A 50–1000 bp ladder (BioVentures, Inc., Murfreesboro, Tenn., USA) was used as a molecular size marker.

V. DNA Hybridization/Colorimetric Detection

Each of the amplified products ($1 \times 10^{12}$ molecules) was diluted in 25 µl of PBS, pH 7.25, and added with 25 µl denaturing solution (0.8N NaOH) to a probe-coated well. After incubation for 10 minutes at room temperature, 25 µl 4X hybridization solution (PBS, pH 7.25, 8% BSA) and 25 µl neutralizing solution (4M Ammonium Acetate)(Sigma Chemical Co., St. Louis, Mo., USA) were added and incubated for a further 5 minutes at room temperature. The plate was then incubated for 45 minutes at 55° C. Following incubation, the plate was washed 5 times with wash buffer (1M Tris-buffered saline, pH 7.5, 1.0% Tween 20) at room temperature. For colorimetric analysis of the hybridized products bound to the wells, 100 µl of streptavidin-alkaline phosphatase conjugate (SPA, Milan, Italy) was added and incubated for 30 minutes at 37° C. The plate was washed 5 times with wash buffer and incubated a further 30 minutes at 37° C. in 100 µl p-NPP solution (1 mg/ml p-nitrophenyl phosphate in 0.5M Tris, pH 9.5). The reaction was stopped with the addition of 1.5N NaOH. Absorbance values were determined by analysis at 405 nm on a SLT Labinstruments Model #16-886 microplate reader (SLT, Salzburg, Austria).

RESULTS

As seen in Table 11, the modified probes used to discriminate between the uidA allele of the O157:H7 *E. coli* and the O25:K98:NM *E. coli* strains substitute inosine molecules for guanosine and cytosine in varying locations. Because guanosine and cytosine affect strong triple bonds, substitution of these bases with the neutral base, inosine, was anticipated to have the most effect. The probes were designed by varying the placement and number of inosines in a given DNA sequence. The probe lengths were also modified to maximize the discrimination.

As described above, each probe was covalently linked to a 96-well microtiter plate and then used immediately for hybridization assays. To minimize the possible variability of covalent linking of the probes to the wells, the assays were run in triplicate on each plate and a total of six plates were used for the hybridization studies. The DNA used for hybridization was amplified from either *E. coli* O157:H7 or *E. coli* O25:K98:NM. The 423 bp region amplified corresponded to nucleotides 198–621 of the uidA gene. The amplified DNA sequences were analyzed by migration on a 4% agarose gel. Serial dilutions of the products were quantitated by comparison with a known standard on the gel. The plates were hybridized with equal amounts of amplification products(approximately $1\times10^{12}$ molecules/well). Time course experiments determined that the hybridization signal reached saturation by 45 minutes at 55° C. Accordingly, all experiments were analyzed by hybridization at 55° C. for 45 minutes.

Two parameters were determined to judge the efficacy of discrimination of a given probe. The ratio of O157:H7 signal to O25:K98:NM signal was determined for each probe to establish the discrimination of the probes. The signal achieved with the sequence specific O157:H7 probe (100%), SEQ ID NO:20, was compared to the O157:H7 signal retained by each probe and a percentage value calculated to establish the sensitivity of each probe as a marker for identification of the pathogenic strain. The results of these determinations, calculated for all six experiments, are shown in Table 11.

TABLE 11

EXPERIMENTAL RESULTS

| SEQ ID NO: | Probe Designation | Ratio of O157:H7 to O125:K98:NM absorbance | Percentage of O157:H7 absorbance |
|---|---|---|---|
| 19 | M6  | 0.45 +/− 0.19 | 32  |
| 20 | M7  | 2.19 +/− 0.11 | 100 |
| 21 | M1  | 3.17 +/− 0.37 | 86  |
| 22 | M2  | 5.26 +/− 2.44 | 46  |
| 23 | M3  | 2.56 +/− 0.59 | 66  |
| 24 | M4  | 2.58 +/− 0.70 | 82  |
| 25 | M5  | 3.09 +/− 0.92 | 27  |
| 26 | M8  | 3.55 +/− 0.73 | 63  |
| 27 | M9  | 5.52 +/− 2.69 | 49  |
| 28 | M10 | 3.26 +/− 2.25 | 24  |
| 29 | M11 | 3.05 +/− 0.61 | 73  |
| 30 | M12 | 2.84 +/− 0.32 | 75  |

Based on the selected parameters, the M1 probe exhibits the best discrimination (3.17 +/−0.37) while retaining the best signal (86%). Other probes show excellent discrimination, e.g., probes M2, M8 and M9, however, the variability is increased and the signal is reduced. Substitution of inosine at position 11 and 13 (probes M2, M9, M11, M12, and M3, respectively) demonstrated highly variable or reduced discrimination and a reduced overall signal intensity. Probes M2 and M9 have an inosine substitution immediately downstream to the single base mismatch and both demonstrated reduced signal intensity and high variability of discrimination. The variability was reduced and signal intensity was partially recovered by increasing the length of the probes, e.g., probes M11 and M12. Probe M3, with an inosine substitution at position 13, demonstrated less of an effect on signal intensity but the discrimination was reduced. Substitution of multiple inosines, as in probes M4, M5, and M10, resulted in good discrimination but a reduced signal. Comparisons of probes M9 and M2 to M11 and M12 and comparison of probe M8 to M1 indicates that increasing the length of the probe increases the signal intensity while also stabilizing the variability of the discrimination.

It will be appreciated from the above results that the incorporation of neutral base substitution into sequence-specific probes achieves a sensitivity and efficiency capable of differentiating even single base mismatches between amplified nucleic acid sequences.

The present invention may be embodied or utilized in other specific forms or manners without departing from its spirit or essential characteristics. The described embodiments and methods are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for detecting mismatches between a first nucleic acid sequence and a second nucleic acid sequence wherein said first and second nucleic acid sequences contain at least one base difference, said method comprising the steps of:

obtaining at least one probe consisting of an oligonucleotide sequence spanning the location of at least one base difference between said first and said second nucleic acid sequences, said probe labelled with a label permitting detection of the probe when hybridized to a complementary nucleic acid sequence, said oligonucleotide sequence incorporating at least one neutral base molecule in a position other than the position of the at least one base difference, said oligonucleotide sequence otherwise being exactly complementary to said first nucleic acid sequence such that hybridization of said probe with said second nucleic acid sequence is weakened relative to hybridization of said probe with said first nucleic acid sequence;

mixing said probes and said first and second nucleic acid sequences under hybridization conditions;

effecting disassociation of a substantial proportion of hybrids comprising said probe and said second nucleic acid sequences, if present; and detecting hybrids comprising said probe and said first nucleic acid sequence.

2. A kit useful for detecting mismatches between a first nucleic acid sequence and a second nucleic acid sequence wherein said first and second nucleic acid sequences contain at least one base difference, said kit comprising at least one probe consisting of an oligonucleotide sequence spanning the location of the at least one base difference between said first and said second nucleic acid sequences, said probe labelled with a label permitting detection of the probe when hybridized to a complementary nucleic acid sequence, said oligonucleotide sequence incorporating at least one neutral base molecule in a position other than the position of the at least one base difference, said oligonucleotide sequence otherwise being exactly complementary to said first nucleic acid sequence.

\* \* \* \* \*

UNITED STATES PATENT AND TRADEMARK OFFICE
CERTIFICATE OF CORRECTION

PATENT NO. : 5,753,444
DATED : May 19, 1998
INVENTOR(S) : Linxian Wu; Jana Coombs; Sharon L. Malmstrom; Michael J. Glass It is certified that error appears in the above-identified patent and that said Letters Patent is hereby corrected as shown below:

Title page, Right Column, line 1, after "Stone, G.," change "Oberts" to --Oberst--

Col. 5, line 24, after "means" change "Which" to --which--

Col. 8, line 24, after "and" change "mmucus" to --mucus--

Col. 10, line 57, after "performed." insert a paragraph break

Col. 16, line 47, after "#J00172," insert --#J00173, #J00174, #J00175, #J00177,--

Signed and Sealed this

Twenty-third Day of March, 1999

Attest:

Q. TODD DICKINSON

*Attesting Officer*     *Acting Commissioner of Patents and Trademarks*